United States Patent
Nilvebrant et al.

(10) Patent No.: US 6,630,162 B1
(45) Date of Patent: *Oct. 7, 2003

(54) PHARMACEUTICAL FORMULATION AND ITS USE

(75) Inventors: Lisbeth Nilvebrant, Bromma (SE); Bengt Hallen, Sollentuna (SE); Birgitta Olsson, Stenhamra (SE); Jan Strombom, Vattholm (SE); Torkek Gren, Kalamazoo, MI (US); Anders Ringberg, Stockholm (SE); Martin Wikberg, Kullavik (SE)

(73) Assignee: Pharmacia AB, Stockholm (SE)

(*) Notice: Subject to any disclaimer, the term of this patent is extended or adjusted under 35 U.S.C. 154(b) by 0 days.

This patent is subject to a terminal disclaimer.

(21) Appl. No.: 09/708,428

(22) Filed: Nov. 9, 2000

Related U.S. Application Data

(63) Continuation-in-part of application No. PCT/SE99/02052, filed on Nov. 11, 1999.
(60) Provisional application No. 60/202,862, filed on May 10, 2000.

(30) Foreign Application Priority Data

Mar. 9, 2000 (SE) ................................................ 0000782

(51) Int. Cl.$^7$ .............................. A61K 9/52; A61K 9/54; A61K 9/26; A61K 9/16; A61K 9/22

(52) U.S. Cl. ...................... 424/458; 424/457; 424/459; 424/461; 424/462; 424/468; 424/469; 424/490; 424/493; 424/494; 424/495

(58) Field of Search .................................. 424/457, 458, 424/459, 461, 462, 468, 469, 490, 493, 494, 495

(56) References Cited

U.S. PATENT DOCUMENTS

| | | | |
|---|---|---|---|
| 5,382,600 | A | 1/1995 | Jonsson et al. |
| 5,559,269 | A | 9/1996 | Johansson et al. |

FOREIGN PATENT DOCUMENTS

| | | |
|---|---|---|
| EP | 0061217 | 9/1982 |
| WO | WO9323025 | 11/1993 |
| WO | WO9601621 | 1/1996 |
| WO | WO9612477 | 5/1996 |
| WO | WO9629992 | 10/1996 |
| WO | WO 98/03067 | * 1/1998 |
| WO | WO9803067 | 1/1998 |
| WO | WO9811888 | 3/1998 |
| WO | WO0012069 | 3/2000 |
| WO | WO0027364 | 5/2000 |

OTHER PUBLICATIONS

Nilvebrant et al., *Euro. J. Pharmacology*, vol. 327 (1997) pp. 195–207.
Brynne et al., *Int'l J. Clin. Pharmacology and Therapeutics*, vol. 35, No. 7 (1997) pp. 287–295.
Nilvebrant et al., *Life Sciences*, vol. 60, Nos. 13/14 (1997) pp. 1129–1136.
Stahl et al., *Neurourology and Urodynamics*, vol. 14, (1995) pp. 647–655.

* cited by examiner

Primary Examiner—Thurman K. Page
Assistant Examiner—Todd D Ware
(74) Attorney, Agent, or Firm—Craig M. Bell

(57) ABSTRACT

The invention relates to a pharmaceutical formulation containing tolterodine or a tolterodine-related compound, or a pharmacologically acceptable salt thereof, as active ingredient, in which the formulation exhibits a controlled in vitro release of the active ingredient in phosphate buffer at pH 6.8 of not less than about 80% after 18 hours, and after oral administration to a patient is capable of maintaining a substantially constant serum level of the active moiety or moieties for 24 hours. The invention also relates to the use of the pharmaceutical formulation for treating overactive bladder and gastrointestinal disorders.

23 Claims, 1 Drawing Sheet

PHARMACEUTICAL FORMULATION AND ITS USE

Figure 1:
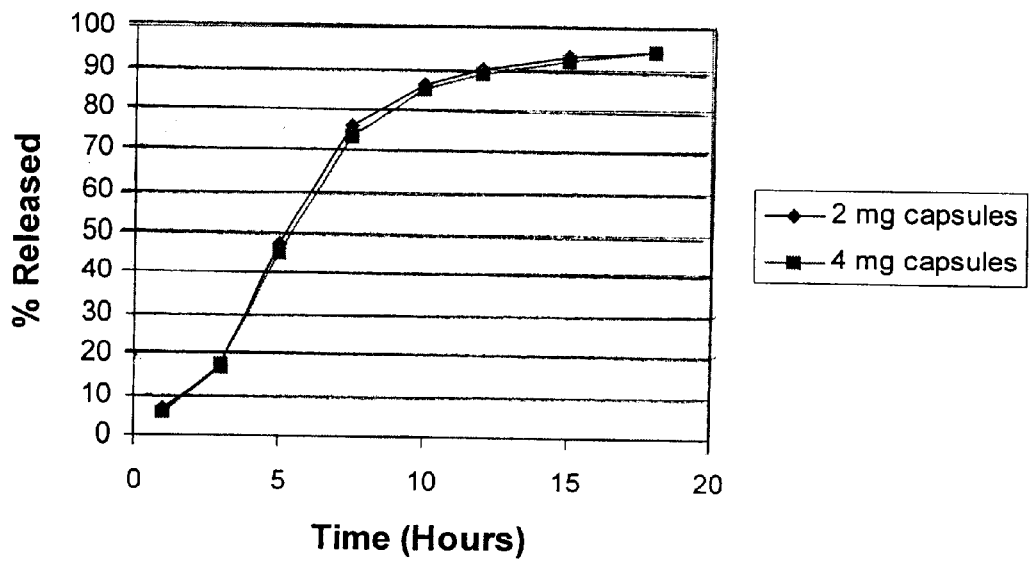

This application is a continuation-in-part of PCT international application No. PCT/SE99/02052 which has an international filing date of Nov. 11, 1999 and which designated the United States, the entire contents of which are hereby incorporated by reference. This application also claims priority under 35 U.S.C. 119(e) of U.S. Provisional No. 60/202,862, filed on May 10, 2000, the entire contents of which are also hereby incorporated by reference.

The present invention relates to a pharmaceutical formulation for administering tolterodine or a tolterodine-related compound, and to the medical use of such a formulation.

A substantial part (5–10%) of the adult population suffers from overactive or unstable urinary bladder, often also referred to as urinary incontinence. The symptoms of an unstable or overactive bladder comprise urge incontinence, urgency and urinary frequency. The prevalence of overactive bladder, particularly of so-called urge incontinence, increases with age. It is assumed that unstable or overactive bladder is caused by uncontrolled contractions of the bundles of smooth muscle fibres forming the muscular coat of the urinary bladder (the detrusor muscle) during the filling phase of the bladder. These contractions are mainly controlled by cholinergic muscarinic receptors, and the pharmacological treatment of unstable or overactive bladder has been based on muscarinic receptor antagonists. The drug of choice has for a long time been oxybutynin.

Recently, however, an improved muscarinic receptor antagonist, tolterodine, (R)-N,N-diisopropyl-3-(2-hydroxy-5-methylphenyl)-3-phenylpropanamine, has been marketed for the treatment of urge incontinence and other symptoms of unstable or overactive urinary bladder. Both tolterodine and its major, active metabolite, the 5-hydroxymethyl derivative of tolterodine, which significantly contributes to the therapeutic effect, have considerably less side-effects than oxybutynin, especially regarding the propensity to cause dry mouth. While tolterodine is equipotent with oxybutynin in the bladder, its affinity for muscarinic receptors of the salivary gland is eight times lower than that of oxybutynin; see, for example, Nilvebrant, L., et al., European Journal of Pharmacology 327 (1997) 195–207. The selective effect of tolterodine in humans is described in Stahl, M. M. S., et al., Neurourology and Urodynamics 14 (1995) 647–655, and Bryne, N., International Journal of Clinical Pharmacology and Therapeutics, Vol. 35, No. 7 (1995) 287–295.

The currently marketed administration form of tolterodine is filmcoated tablets containing 1 mg or 2 mg of tolterodine L-tartrate for immediate release in the gastrointestinal tract, the recommended dosage usually being 2 mg twice a day. While, as mentioned, the side-effects, such as dry mouth, are much lower than for oxybutynin, they still exist, especially at higher dosages.

Our co-pending international application PCT/SE99/01463 relates to the administration of tolterodine and tolterodine-related compounds through a controlled release formulation and is based on the finding that, contrary to the case of oxybutynin, the substantial elimination of peak serum levels of tolterodine and its active metabolite through controlled release of tolterodine for an extended period of time, such as through a once-daily administration form, while maintaining the desired effect on the bladder, indeed gives a significant reduction of the (already low) side-effects, particularly dry mouth, compared with those obtained for the same total dosage of immediate release tablets over the same period. In other words, eliminating the peak serum levels of the active moiety affects the adverse effects, and particularly dry mouth, more than the desired effect on the detrusor activity, simultaneously as the flattening of the serum concentration does not lead to loss of activity or increased incidence of urinary retention or other safety concerns. Thus, in addition to the convenience advantage of controlled release administration, one may either (i) for a given total dosage of tolterodine, reduce the side-effects, such as dry mouth, or (ii) for a given level of acceptable side-effects, increase the dosage of tolterodine to obtain an increased effect on the bladder, if desired.

Our above-mentioned PCT/SE99/01463 discloses treatment of overactive bladder by the administration of a controlled release formulation that delivers tolterodine, a tolterodine-related compound, or a pharmacologically acceptable salt thereof such that a substantially constant serum level of the active moiety or moieties is maintained for at least 24 hours.

The present invention is based on the unexpected observation that a substantially constant serum level of the active moiety or moieties for 24 hours may be obtained through oral administration of a controlled release pharmaceutical formulation that releases the major content of active compound in less than about 18 hours, and more particularly that the formulation has an in vitro release of not less than about 80% after 18 hours at the conditions specified below.

In one aspect, the present invention therefore provides a pharmaceutical formulation containing tolterodine or a tolterodine-related compound, or a pharmacologically acceptable salt thereof, as active ingredient, in which the formulation exhibits a controlled in vitro release of the active ingredient in phosphate buffer at pH 6.8 of not less than about 80% after 18 hours, and after oral administration to a patient is capable of maintaining a substantially constant serum level of the active moiety or moieties for 24 hours.

A second aspect of the invention relates to the use of the pharmaceutical formulation for treating a disorder or disease selected from overactive bladder (including i.a. urinary incontinence and nocturia) and gastrointestinal disorders.

A third aspect of the invention relates to the use of tolterodine or a tolterodine-related compound, or a pharmacologically acceptable salt thereof, for the preparation of the pharmaceutical formulation of the above first aspect of the invention.

Preferably, the fraction of tolterodine, tolterodine-related compound or salt thereof that is released is not less than about 80% after 15 hours, especially not less than about 80% after 12 hours.

On the other hand, the fraction of tolterodine, tolterodine-related compound or salt thereof that is released in vitro after 1 hour is preferably not more than about 50%, especially not more than about 30%.

The fraction of tolterodine, tolterodine-related compound or salt thereof that is released in vitro after three hours is preferably from about 30 to 95%, especially from about 40 to about 85%.

It may be preferred that after 7 hours, the fraction of tolterodine, tolterodine-related compound or salt thereof that is released in vitro is not less than about 50%, especially not less than about 80%.

In an exemplary in vitro release profile for the pharmacutical formulation, the fraction of tolterodine, tolterodine-related compound or salt thereof that is released in vitro is less than about 50% after 1 hour, from about 30 to about 95% after 3 hours, and more than about 50% after 7 hours.

The in vitro release measurement conditions referred to above are those for a drug release test that utilizes the United States Pharmacopea (USP) Apparatus 1 (rotating basket) at 100 rpm with 900 ml of deareated phosphate buffer at pH 6.8 and 37° C., where the phosphate buffer solution is prepared as described on pages 2049–2050 in USP 23. The phosphate buffer nominally contains 0.05 M phosphate.

By the term "active moiety or moities" it is meant, in the case of tolterodine and its related compounds, the sum of free or unbound (i.e. not protein bound) concentrations of (i) tolterodine and active metabolite thereof, when tolterodine (or prodrug form) is administered; or (ii) tolterodine and active metabolite thereof and/or (S)-enantiomer to tolterodine and active metabolite thereof, when the corresponding racemate (or prodrug form) is administered; or (iii) active metabolite, when the (R)-5-hydroxymethyl metabolite of tolterodine (or prodrug form) is administered; or (iv) (S)-enantiomer to tolterodine and active metabolite thereof, when the (S)-enantiomer (or prodrug) is administered; or (v) active (S)-metabolite, when the (S)-5-hydroxymethyl metabolite is administered.

The term "substantially constant" with respect to the serum level of active moiety or moieties means that the serum profile after administration of the controlled release formulation does essentially not exhibit any substantial peak values. This may also be expressed mathematically by reference to the "fluctuation index" (FI) for the serum concentration of (unbound) active moiety (or sum of active moities when relevant), where the fluctuation index FI is calculated as $$FI=(C\text{max}-C\text{min})/AUC\tau/\tau$$

wherein Cmax and Cmin are the maximum and minimum concentrations, respectively, of active moiety, $AUC\tau$ is the area under the serum concentration profile (concentration vs time curve), and $\tau$ is the length of the dosage interval during the time $\tau$. The controlled release formulation according to the present invention readily permits a mean fluctuation index (for n being at least 30) that is not higher than about 2.0, more preferably not higher than about 1.5, particularly not higher than about 1.0, for example not higher than about 0.8.

For tolterodine and its 5-hydroxymethyl metabolite, the 24-hour exposure, expressed as AUC unbound active moiety (tolterodine plus metabolite) is usually in the range of from about 5 to about 150 nM*h, preferably from about 10 to about 120 nM*h, depending on the dosage needed by the particular patient. The indicated limits are based upon calculation of the unbound concentrations of active moiety assuming a fraction unbound of 3.7% for tolterodine and 36% for the 5-hydroxymethyl metabolite (Nilvebrant, L., et al., Life Sciences, Vol. 60, Nos. 13/14 (1997) 1129–1136).

Correspondingly, for tolterodine and its 5-hydroxymethyl metabolite, the average unbound (blood) serum or plasma levels of active moiety (tolerodine plus metabolite) are usually in the range of about 0.2 to about 6.3 nM, preferably in the range of about 0.4 to about 5.0 nM.

The formulation of the present invention is not restricted to any particular type of formulation. Thus, various types of controlled or sustained release type formufations may be used for embodying the present invention, such as, for example, osmotic tablets, gel matrix tablets, coated beads, etc.

A common type of controlled release formulation that may be used for the purposes of the present invention comprises an inert core, such as a sugar sphere, coated with an inner drug-containing layer and an outer membrane layer controlling drug release from the inner layer. A "sealcoat" may be provided between the inert core and the layer containing the active ingredient. When the core is of a water-soluble or water-swellable inert material, the sealcoat is preferably in the form of a relatively thick layer of a water-insoluble polymer. Such a controlled release bead may thus comprise:

(i) a core unit of a substantially water-soluble or water-swellable inert material;
  (ii) a first layer on the core unit of a substantially water-insoluble polymer;
  (iii) a second layer covering the first layer and containing an active ingredient; and
  (iv) a third layer on the second layer of polymer effective for controlled release of the active ingredient,
    wherein the first layer is adapted to control water penetration into the core.

The term "control water penetration into the core" as used above means that the water influx to the core should be retarded in a controlled manner to such an extent that the drug release profile will be altered in a predictable fashion. Thus, while in many cases it may be preferred that the water penetration into the core is substantially or completely eliminated, a certain, controlled influx of water to the core may be acceptable in other cases.

The above-mentioned first layer of water-insoluble material may also serve to provide mechanical integrity to the core.

Optionally, the above-mentioned third, or controlled release layer is coated with one or more additional layers of water-soluble or insoluble polymer, e.g. a non-thermoplastic soluble polymer to decrease tackiness of the beads for subsequent processing, such as curing and filling into capsules, or a secondary functional coating, such as an enteric coating that delays the onset of drug release. Optionally, such an additional layer may contain drug for immediate release.

Usually, the first layer (ii) above constitutes more than about 2% (w/w) of the final bead composition, preferably more than about 3% (w/w), e.g. from about 3% to about 80% (w/w).

The amount of the second layer (ii) above usually constitutes from about 0.05 to about 60% (w/w), preferably from about 0.1 to about 30% (w/w) of the final bead composition.

The amount of the third layer (iv) above usually constitutes from about 1 to about 50% (w/w), preferably from about 2 to about 25% (w/w) of the final bead composition.

The core unit typically has a size in the range of from about 0.05 to about 2 mm.

The controlled release beads may be provided in a multiple unit formulation, such as a capsule or a tablet.

The cores are preferably of a water-soluble or swellable material, and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose.

The substantially water-insoluble material in the first, or sealcoat layer is generally a "GI insoluble" or "GI partially insoluble" film forming polymer (dispersed or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone (PVP), polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethylhydroxyethyl cellulose, acrylic acid polymers, polymethacrylates, or any other pharmaceutically acceptable polymer.

The ratio of drug to hydrophilic polymer in the second layer is usually in the range of from 1:100 to 100:1 (w/w).

Suitable polymers for use in the third layer, or membrane, for controlling the drug release may be selected from water-insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above. Optionally, the controlled release layer comprises, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

The above controlled release beads and formulation, respectively may be produced by a method comprising the following steps:

a) providing a core unit of a substantially water-soluble or water-swellable material;

b) applying a first layer of a substantially water-insoluble polymer to said core;

c) applying onto said first layer, a second layer comprising an active ingredient and optionally a polymer binder; and d) applying onto said second layer, a third polymer layer effective for controlled release of the active ingredient; wherein the amount of material in said first layer is selected to provide a layer thickness that permits control of water penetration into the core.

Optionally, one or more additional polymer layers are applied to the core as has been mentioned above.

The preparation of the multiple unit formulation comprises the additional step of transforming the prepared beads into a pharmaceutical formulation, such as by filling a predetermined amount of the beads into a capsule, or compressing the beads into tablets.

The layering or coating operations are preferably performed by spraying a solution or dispersion of the respective layer materials onto the core, preferably in a fluid bed coating apparatus.

After the final coating step, the beads are optionally "cured", usually in a fluid bed system or in a tray dryer system, by heating to a temperature of about 30–80° C., for 30 to 180 minutes, for example. Suitably, the beads are then cooled below about 35° C. before stopping the process.

As mentioned above, the pharmaceutical formulation according to the present invention may be used for treating, inter alia, urinary disorders including overactive urinary bladder. The overactive bladder condition gives rise to urinary frequency, urgency and/or urge incontinence. Overactive bladder disorders also include nocturia, i.e. awakening at night to urinate. While overactive bladder is often associated with detrusor muscle instability, disorders of bladder function may also be due to neuropathy of the central nervous system (detrusor hyperreflexia) including spinal cord and brain lesions, such as multiple sclerosis and stroke. Overactive bladder symptoms may also result from, for example, male bladder outlet obstruction (usually due to prostatic hypertrophy), interstitial cystitis, local edema and irritation due to focal bladder cancer, radiation cystitis due to radiotherapy to the pelvis, and cystitis. The formulation may also be useful for treating gastrointestinal disorders, including gastrointestinal hyperactivity.

The pharmaceutical formulation according to the present invention has proved to be very suitable for administering the above-mentioned drug tolterodine, the chemical name of which is (R)-N,N-diisopropyl-3-(2-hydroxy-5-methylphenyl)-3-phenylpropanamine, and would likewise be suitable for its related compounds, i.e. the major, active metabolite of tolterodine, i.e. (R)-N,N-diisopropyl-3-(2-hydroxy-5-hydroxymethylphenyl)-3-phenylpropanamine; the corresponding (S)-enantiomer to tolterodine, i.e. (S)-N,N-diisopropyl-3-(2-hydroxy-5-methylphenyl)-3-phenylpropanamine; the 5-hydroxymethyl metabolite of the (S)-enantiomer, i.e. (S)-N,N-diisopropyl-3-(2-hydroxy-5-hydroxymethylphenyl)-3-phenylpropanamine; as well as the corresponding racemate to tolterodine, i.e. (R,S)-N,N-diisopropyl-3-(2-hydroxy-5-methylphenyl)-3-phenylpropanamine; and prodrug forms and pharmacologically acceptable salts thereof.

Tolterodine is marketed for the treatment of unstable or overactive urinary bladder with symptoms including urinary incontinence (urge incontinence), urgency and urinary frequency. The 5-hydroxymethyl metabolite of tolterodine mentioned above contributes significantly to the therapeutic effect of tolterodine.

Tolterodine, its corresponding (S)-enantiomer and racemate and the preparation thereof are described in e.g. the above-mentioned U.S. Pat. No. 5,382,600. For a description of the active (R)-5-hydroxymethyl metabolite of tolterodine (as well as the (S)-5-hydroxymethyl metabolite), it may be referred to the above-mentioned U.S. Pat. No. 5,559,269. The (S)-enantiomer, its non-cholinergic spasmolytic activity and use in the treatment of urinary and gastrointestinal disorders are described in WO 98/03067.

Figure 2:
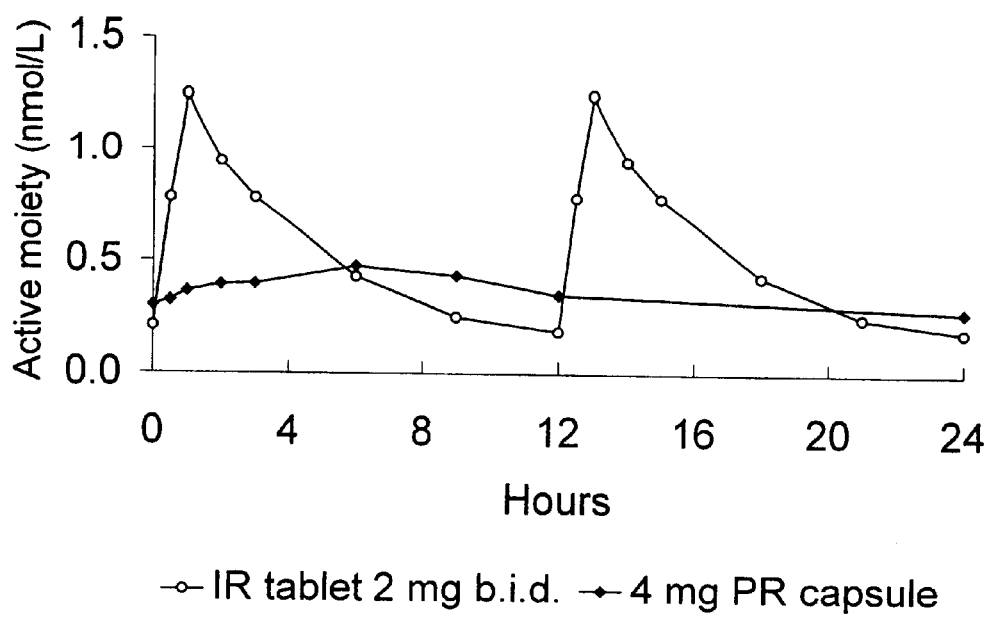

The invention will now be described in more detail by the following non-limiting Examples. Reference will be made to the accompanying drawings, wherein:

FIG. 1 is a diagram showing the fraction of tolterodine L-tartrate released in vitro versus time for 2 and 4 mg controlled release capsules according to the Example below; and FIG. 2 is a diagram showing the variation of serum concentration (nmol/L) of (unbound) active moiety with time (hours) during 24 hours when administering a predetermined total dosage of tolterodine (4 mg) through a prolonged release (PR) capsule (4 mg) according to the Example below once daily. The corresponding variation with a prior art immediate release (IR) tablet (2 mg) twice daily is also shown.

EXAMPLE

Preparation of Controlled Release Beads and Capsules

An exemplary bead formulation containing tolterodine L-tartrate as active ingredient has the following structure:

| | |
|---|---|
| Core: | Starch-containing sugar sphere of about 0.8 mm diameter (commercially available); comprises 73% w/w of the final bead; purpose: coating substrate; |
| First layer: | Surelease ® "sealcoat" (Surelease ® is an aqueous film-coating dispersion, about 25% solids, consisting primarily of ethylcellulose plasticized with fractionated coconut oil, and manufactured by Colorcon, Inc, USA); comprises about 12% w/w of the final bead; purpose: to provide more consistent core surface; during drug release phase maximize time that drug is saturated inside bead and minimize osmotic effects; control drug release rate together with the third layer; |
| Second layer: | Tolterodine L-tartrate/hydroxypropylmethylcellulose (HPMC); comprises about 3% w/w of the final bead; ratio of Tolterodine:HPMC is 5:1; purpose: drug supply; |
| Third layer: | Surelease ®/HPMC; comprises about 12% w/w of the final bead; ratio of Surelease ®:HPMC is 6:1; purpose: drug release rate control; |

Beads with a three-layer coating having the above characteristics were prepared as follows:

1200 g of sugar spheres, 20–25 mesh, were charged into a Wurster fluid bed and sequentially coated at a nominal product temperature of 36 to 40° C. with the following three coating liquids:

(1) a Surelease® sealcoating liquid prepared by mixing 788 g of Surelease® with 563 g of purified water;
(2) a drug-containing solution prepared by first dissolving 35.0 g of tolterodine L-tartrate in 2190 g of purified water, and then mixing the solution with 6.6 g of hydroxypropylmethyl cellulose (HPMC) 5 cP; and
(3) a sustained release coating liquid prepared by mixing 29 g of HPMC 5 cP with 375 g of purified water, and then mixing with 695 g of Surelease®.

After tray drying for 3 hours at 70° C., the coated spheres were filled into size #4 or size #3 hard gelatin capsules to obtain 2 mg and 4 mg tolterodine L-tartrate capsules, respectively, of the composition:

| | 2 mg capsule | 4 mg capsule |
|---|---|---|
| Tolterodine L-tartrate | 2.0 mg | 4.0 mg |
| sugar spheres, 20–25 mesh | 68.6 mg | 137.2 mg |
| Surelease ® | 21.2 mg | 42.4 mg |
| HPMC 5cP | 2.0 mg | 4.0 mg |

Optionally, a fourth layer may be applied to the bead before drying by Wurster coating.

| | |
|---|---|
| Fourth layer: | HPMC; comprises about 1% w/w of the final bead; purpose: decrease tackiness of beads for subsequent processing (curing and capsule filling). |

In the case of the above described bead, such a fourth layer may be applied with a coating solution prepared by dissolving 16.4 g of HPMC in 234 g of water.

Drug In Vitro Release Study

A drug-release test which utilizes the USP Apparatus 1 (rotating basket) at 100 rpm with 1000 mL of deaerated phosphate buffer prepared at pH 6.8, was used to study the in vitro release at 37° C. of the two three-layered beads-containing 2 and 4 mg capsules prepared above. The buffer was identical to that used for the Buffer Stage testing of Delayed-release dosage forms described in USP 23 General Chapter 724, and nominally contains 0.05 M phosphate and 0.075 M chloride. The results are shown in FIG. 1. As can be seen therein, about 90% of the tolterodine tartrate had been released from both capsules after 12 hours.

Pharmacokinetic Study—Determination of Serum Concentrations of Tolterodine and Main Metabolite A clinical trial was performed in patients with overactive bladder to determine the pharnacokinetic effects of a (i) a once daily dose of a 4 mg tolterodine controlled release capsule (below referred to as TOD) as described above, and (ii) two doses daily of a tolterodine immediate release tablet (below referred to as TIR), described below. 30 patients were subjected to each of the treatments. The measurements were performed on day seven in each treatment period and included measurements of serum concentrations of tolterodine and its main 5-hydroxymethyl metabolite (below called 5-HM) over time.

Blood samples were drawn immediately before dosing and after 0.5, 1, 2, 3, 6, 9, 12, 24 and 25 hours, and the free (unbound) serum concentrations of tolterodine and its 5-HM metabolite were measured by gas chromatography/mass spectrometry. The unbound concentrations were calculated assuming a fraction unbound of 3.7% for tolterodine and of 36% for 5-HM as obtained from protein binding studies on human 25 serum (Nilvebrant, L., et al., Life Sciences, Vol. 60, Nos. 13/14 (1997) 1129–1136). FIG. 2 shows the obtained variation with time of the sum of the unbound concentrations of tolterodine and 5-HM (which sum is referred to as "active moiety") for, on the one hand, the administration of a 4 mg TOD capsule once daily (PR capsule in FIG. 2), and, on the other hand, the administration of a 2 mg TIR tablet twice daily (i.e. equivalent 24-hour doses of capsule and tablet). As shown in the Figure, the peaks obtained with the TIR tablet are eliminated with the TOD capsule, the latter thus providing a substantially constant serum concentration of active moiety during the 24 hours illustrated.

The difference in fluctuation of the serum concentrations between TIR tablet and TOD capsule may also be demonstrated by calculation of the "fluctuation index". The fluctuation index, FI, is calculated as $FI=(C_{max}-C_{min})/AUC\tau/\tau$, where $\tau$ is the length of the dosage interval and $AUC\tau$ is the area under the serum concentration profile during a dosage interval. Thus, the mean calculated fluctuation index for the active moiety was 2.29 (95% CI 1.95–2.63) for the TIR tablet (based on n=28), and 0.68 (95% CI 0.59–0.78) for the TOD capsule.

While the invention has been described above with reference to specific embodiments thereof, it is not restricted thereto in any way whatsoever. On the contrary, as will be understood by those skilled in the art, various changes, modifications, substitutions and omissions can be made without departing from the basic concept of the invention as defined in the claims which follow. Thus, for example, other sustained release formulations may be used.

What is claimed is:

1. An oral pharmaceutical formulation containing tolterodine or a tolterodine-related compound, or a pharmaceutically acceptable salt thereof, as active ingredient, wherein said formulation exhibits controlled in vitro release of the active ingredient in phosphate buffer at pH 6.8 of not less than about 80% after 18 hours, and after oral administration to a patient is capable of maintaining a substantially constant serum level of the active moiety or moieties for 24 hours, and wherein the controlled release formulation provides a mean fluctuation index of said serum level of active moiety or moieties that is not higher than about 2.0, said fluctuation index, FI, being defined as FI=(Cmax−Cmin)/AUC$\tau$/$\tau$, wherein Cmax and Cmin are the maximum and minimum concentrations, respectively, of active moiety or moieties, AUC$\tau$ is the area under the serum concentration profile, and $\tau$ is the length of the dosage interval.

2. The formulation according to claim 1, wherein the fraction of tolterodine, tolterodine-related compound or salt thereof that is released in vitro is not less than about 80% after 15 hours.

3. The formulation according to claim 1, wherein the fraction of tolterodine, tolterodine-related compound or salt thereof that is released in vitro is not less than about 80% after 12 hours.

4. The formulation according to claim 1, wherein the fraction of tolterodine, tolterodine-related compound or salt thereof that is released in vitro is less than about 50% after 1 hour.

5. The formulation according to claim 4, wherein the fraction of tolterodine, tolterodine-related compound or salt thereof that is released in vitro is less than about 30% after 1 hour.

6. The formulation according to claim 1, wherein the fraction of tolterodine, tolterodine-related compound or salt thereof that is released in vitro is from about 30 to about 95% after 3 hours.

7. The formulation according to claim 1, wherein the fraction of tolterodine, tolterodine-related compound or salt thereof that is released in vitro is from about 40 to about 85% after 3 hours.

8. The formulation according to claim 1, wherein the fraction of tolterodine, tolterodine-related compound or salt thereof that is released in vitro is more than about 50% after 7 hours.

9. The formulation according to claim 1, wherein the fraction of tolterodine, tolterodine-related compound or salt thereof that is released in vitro is more than about 80% after 7 hours.

10. The formulation according to claim 1, wherein the fraction of tolterodine, tolterodine-related compound or salt thereof that is released in vitro is not more than about 50% after 1 hour, from about 30 to about 95% after 3 hours, and not less than about 50% after 7 hours.

11. The formulation according to claim 1, wherein the in vitro release is measured by a drug release test which utilizes the United States Pharmacopea (USP) Apparatus 1 (rotating basket) at 100 rpm with 900 ml of deaerated phosphate buffer at pH 6.8 and 37° C., where the phosphate buffer solution is prepared as described on pages 2049–2050 of USP 23, and nominally contains 0.05 M phosphate.

12. The formulation according to claim 1, which comprises tolterodine, its 5-hydroxymethyl metabolite or the racemate corresponding to tolterodine, or a salt thereof.

13. The formulation according to claim 1, which comprises tolterodine, or a salt thereof.

14. The formulation according to claim 1, wherein the 24-hour serum profile, expressed as the AUC of unbound tolterodine and 5-hydroxymethyl metabolite, is from 5 to about 150 nM*h.

15. The formulation according to claim 14, wherein the serum level of unbound tolterodine and 5-hydroxymethyl metabolite is in the range of about 0.2 to about 6.3 nM.

16. A method of treating an overactive bladder, which comprises administering a therapeutically effective amount of a pharmaceutical formulation according to claim 1.

17. A method of treating urinary incontinence, which comprises administering a therapeutically effective amount of a pharmaceutical formulation according to claim 1.

18. A method of treating nocturia, which comprises administering a therapeutically effective amount of a pharmaceutical formulation according to claim 1.

19. A method of treating gastrointestinal disorders, which comprises administering a therapeutically effective amount of a pharmaceutical formulation according to claim 1.

20. A method for orally administering tolterodine or a tolterodine-related compound, or a pharmacologically acceptable salt thereof, to a patient to maintain a substantially constant serum level of the active moiety or moieties for 24 hours, which method comprises administering a pharmaceutical formulation containing tolterodine, a tolterodine-related compound or a salt thereof, which formulation exhibits a controlled in vitro release in phosphate buffer at pH 6.8 of tolterodine, tolterodine-related compound or salt thereof of not less than about 80% after 18 hours.

21. The formulation according to claim 1, wherein the controlled release formulation provides a mean fluctuation index of said serum level of active moiety or moieties that is not higher than about 1.0.

22. The formulation according to claim 15, wherein the 24-hour serum profile, is from about 10 nM*h to about 120 nM*h.

23. The formulation according to claim 16, wherein the serum level of unbound tolterodine and 5-hydroxymethyl metabolite is in the range of about 0.4 to about 5.0 nM.

* * * * *